US00PP35837P2

(12) United States Plant Patent
Gray

(10) Patent No.: US PP35,837 P2
(45) Date of Patent: May 28, 2024

(54) ***CANNABIS* PLANT NAMED 'D1117'**

(50) Latin Name: ***Cannabis* hybrid**
Varietal Denomination: D1117

(71) Applicant: Dewey Scientific, Pullman, WA (US)

(72) Inventor: Michael Rennie Gray, Pullman, WA (US)

(73) Assignee: Dewey Scientific, Pullman, WA (US)

( * ) Notice: Subject to any disclaimer, the term of this patent is extended or adjusted under 35 U.S.C. 154(b) by 0 days.

(21) Appl. No.: 18/189,956

(22) Filed: Mar. 24, 2023

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ..... A01H 5/02; A01H 5/00; A01H 6/28
See application file for complete search history.

(56) References Cited

U.S. PATENT DOCUMENTS

2023/0189677 P1 * 6/2023 Baasch ..... Plt./258

OTHER PUBLICATIONS

Allbud, (2023)."Jamaican Chocolate Marijuana Strain," available online at <https://www.allbud.com/marijuana-strains/sativa-dominant-hybrid/jamaican-chocolate>, 3 pages.
Allbud, (2023)."Mango Sherbet Marijuana Strain" available online at <https://www.allbud.com/marijuana-strains/indica-dominant-hybrid/mango-sherbet>, 3 pages.
Bautista et al., (2021). "Flavonoids in *Cannabis sativa*: Biosynthesis, Bioactivities, and Biotechnology," ACS Omega, 6(8):5119-5123.
Booth et al., (2017). "Terpene synthases from *Cannabis sativa*," Plos One, 12(3):e0173911, 20 pages.
Growdiaries, (2023). "Green Point Seeds: Purple Tahoe," available online at <https://growdiaries.com/seedbank/greenpointseeds/purple-tahoe>, 4 pages.
Kovalchuk et al., (2020). "The genomics of *Cannabis* and its close relatives," Annu. Rev. Plant Biol., 71:713-739.
Leafly, (2023). "G13," available online at <https://www.leafly.com/strains/g-13>, 6 pages.
Leafly, (2023). "Memory Loss," available online at <https://www.leafly.com/strains/memory-loss>, 6 pages.
Leafly, (2023). "Passionfruit Haze—14G Premium Flower," available online at <https://www.leafly.com/brands/west-coast-cure/products/west-coast-cure-passionfruit-haze-14g-premium-flower-flower>, 4 pages.
Leafly, (2023). "Purple Punch," available online at <https://www.leafly.com/strains/purple-punch>, 7 pages.
Leafly, (2023). "Trainwreck," available online at <https://www.leafly.com/strains/trainwreck>, 5 pages.
Mihalyov et al., (2021). "Discovery and Genetic Mapping of PM1, a Powdery Mildew Resistance Gene in *Cannabis sativa* L.," Frontiers in Agronomy, 3:720215, 10 pages.
Zager et al., (2019). "Gene Networks Underlying Cannabinoid and Terpenoid Accumulation in *Cannabis*," Plant Physiology, 180(4):1877-1897.
Unpublished U.S. Appl. No. 18/189,113, filed Mar. 23, 2023, titled "*Cannabis* Plant Named 'D1118'," (Copy not submitted herewith pursuant to the waiver of 37 C.F.R. § 1.98(a)(2)(iii)).
Unpublished U.S. Appl. No. 18/189,958, filed Mar. 24, 2023, titled "*Cannabis* Plant Named 'D586'," (Copy not submitted herewith pursuant to the waiver of 37 C.F.R. § 1.98(a)(2)(iii)).

* cited by examiner

*Primary Examiner* — June Hwu
(74) *Attorney, Agent, or Firm* — Morrison & Foerster LLP

(57) ABSTRACT

A new and distinct variety of *Cannabis* plant named 'D1117', characterized by its distinctly mango-like aroma, its leaf tissue ranging in color from green to dark purple, its block-like calyx structure, and its strong lateral branching pattern, is disclosed.

13 Drawing Sheets

Latin name: Botanical classification: *Cannabis* hybrid.

Varietal denomination: The varietal denomination of the claimed variety of *Cannabis* plant is 'D1117'.

BACKGROUND OF THE INVENTION

*Cannabis* plants have been cultivated for medicinal and recreational purposes for thousands of years. The annual, upright, flowering plants with palmately compound leaves are historically classified into two species. Following this classification, *Cannabis saliva* is tall with long internodes and narrow leaflets, while the shorter, conical *Cannabis indica* is densely branched with broad leaflets. New species classifications have been proposed to address the increased production of *Cannabis* varieties which display features of both historical species, but none have been commonly accepted. Thus, most *Cannabis* varieties sold in the U.S. today continue to he classified as *Cannabis indica, Cannabis saliva*, or *Cannabis* hybrid.

Commercial varieties of *Cannabis* contain floral calyxes and bracts with abundant trichomes. Some types of these hair-like structures (generally referred to as glandular trichomes) secrete cannabinoids and terpenoids, which account for the medicinal and/or psychoactive properties of the plant. Mixtures of these compounds may be separated from the flowers in the form of an oil or resin. Alternatively, the flower buds may be collected and dried to produce marijuana.

Each variety of the *Cannabis* plant has a distinct profile of various cannabinoids and terpenoids that determine its medicinal and/or psychoactive properties. Some varieties have shown potential to relieve nausea, pain, seizures, anxiety, arthritis, and many other medical conditions, with limited psychoactive effects. Other varieties contain high levels of compounds that contribute to dizziness, grogginess, or disorientation. Uplifting or energizing effects have also been observed in some varieties.

*Cannabis* plants present a wide range of potential uses, each requiring a different chemical profile. High or low levels of certain medicinal and/or psychoactive compounds may be desirable for different intended uses. There is therefore a need for new *Cannabis* varieties with new chemical profiles and/or improved characteristics including pest or disease resistance and/or increased yields and/or improved cannabinoid. potency.

SUMMARY OF THE INVENTION

In order to meet these needs, the present invention is directed to an improved variety of *Cannabis* plant. In particular, the present invention relates to a new and distinct *Cannabis* hybrid designated as 'D1117'.

*Cannabis* plant variety 'D1117' was derived from a cross between the female plant 'Mango Sherbet' (unpatented) and the male plant 'Purple Tahoe' (unpatented) in Los Angeles, CA, USA, in March of 2021. The original plant of 'D1117' was first asexually propagated via clonal propagation in Los Angeles, CA, USA in October of 2021.

Subsequent asexual propagation of 'D1117' was conducted by clonal propagation. 'D1117' has undergone testing under greenhouse conditions with supplemental lighting and indoor conditions with full lighting in Los Angeles, CA, USA and Pullman, WA, USA for 16 months. 'D1117' has been found to be stable and reproduce true to type through successive generations of asexual propagations via clonal propagation of apical and side shoots.

'D1117' was particularly selected for its unique aroma, vigor, and cannabinoid potency. In particular, 'D1117' is characterized by its distinctly mango-like aroma, its leaf tissue ranging in color from green to dark purple, its block-like calyx structure, and its strong lateral branching angle (40 degrees). Primary market uses for 'D1117' products are dried flower material and extracts for ingestion. Dried 'D1117' flower material has good shipping quality and storage life. 'D1117' has demonstrated excellent productivity, with each plant producing approximately 140 grams of dry flower material under optimal greenhouse conditions.

BRIEF DESCRIPTION OF THE DRAWINGS

This new *Cannabis* plant variety is illustrated by the accompanying photographs. The colors shown are as true as can be reasonably obtained by conventional photographic procedures, The plants shown were grown from clonal propagates in 2 gallon containers for 10-13 days under a 18 h light/6 h dark cycle and then moved to a 12 h light/12 h dark lighting regime. The photographs were taken 8 weeks after moving the plants to the 12 h light/12 h dark lighting regime, corresponding to 13 weeks after roots emerged on the clonal propagates from which the plants were grown.

DETAILED BOTANICAL DESCRIPTION

Figure 1A:
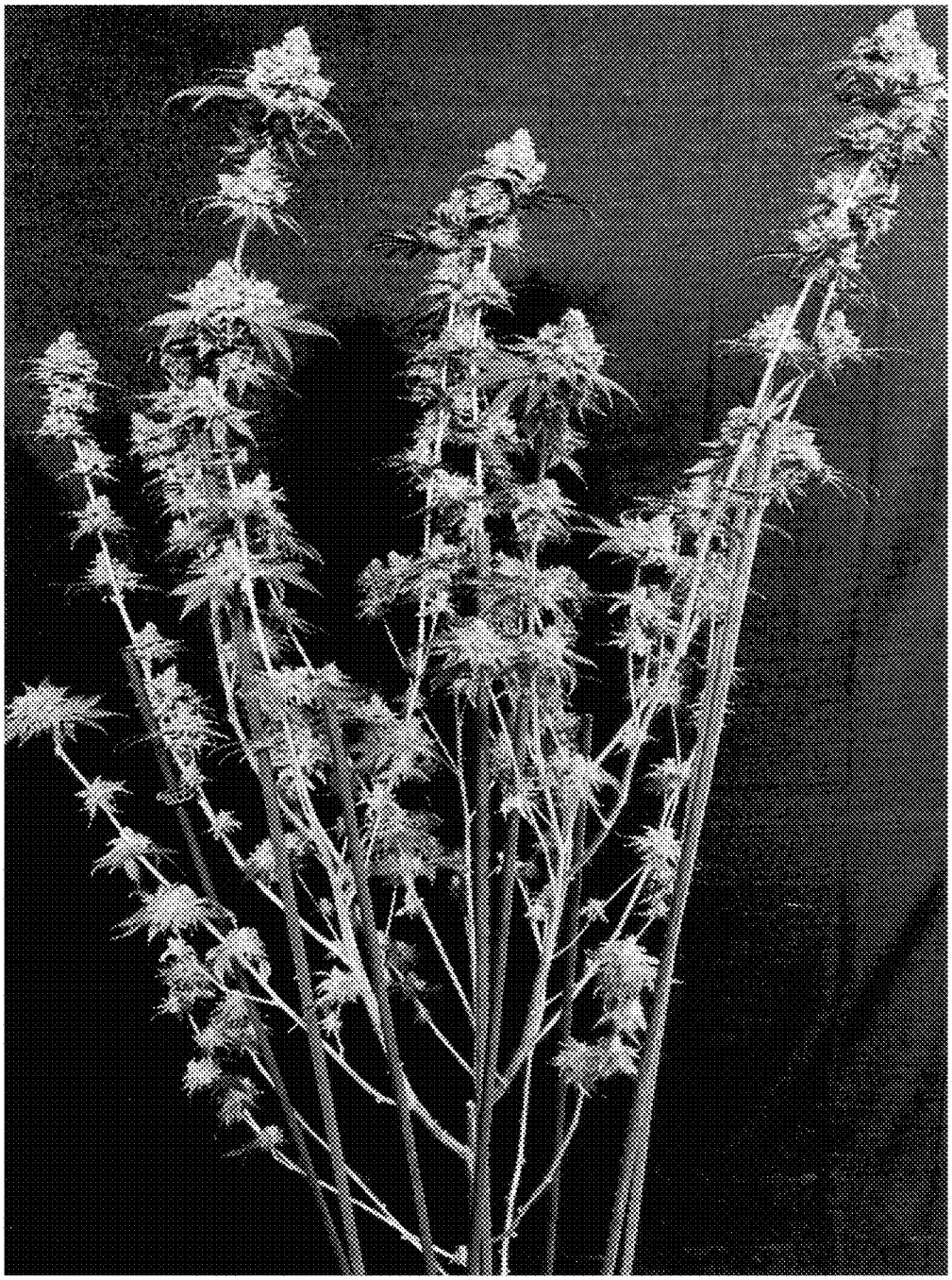
FIG. 1A illustrates a side view of a 'D1117' plant.
Figure 1B:
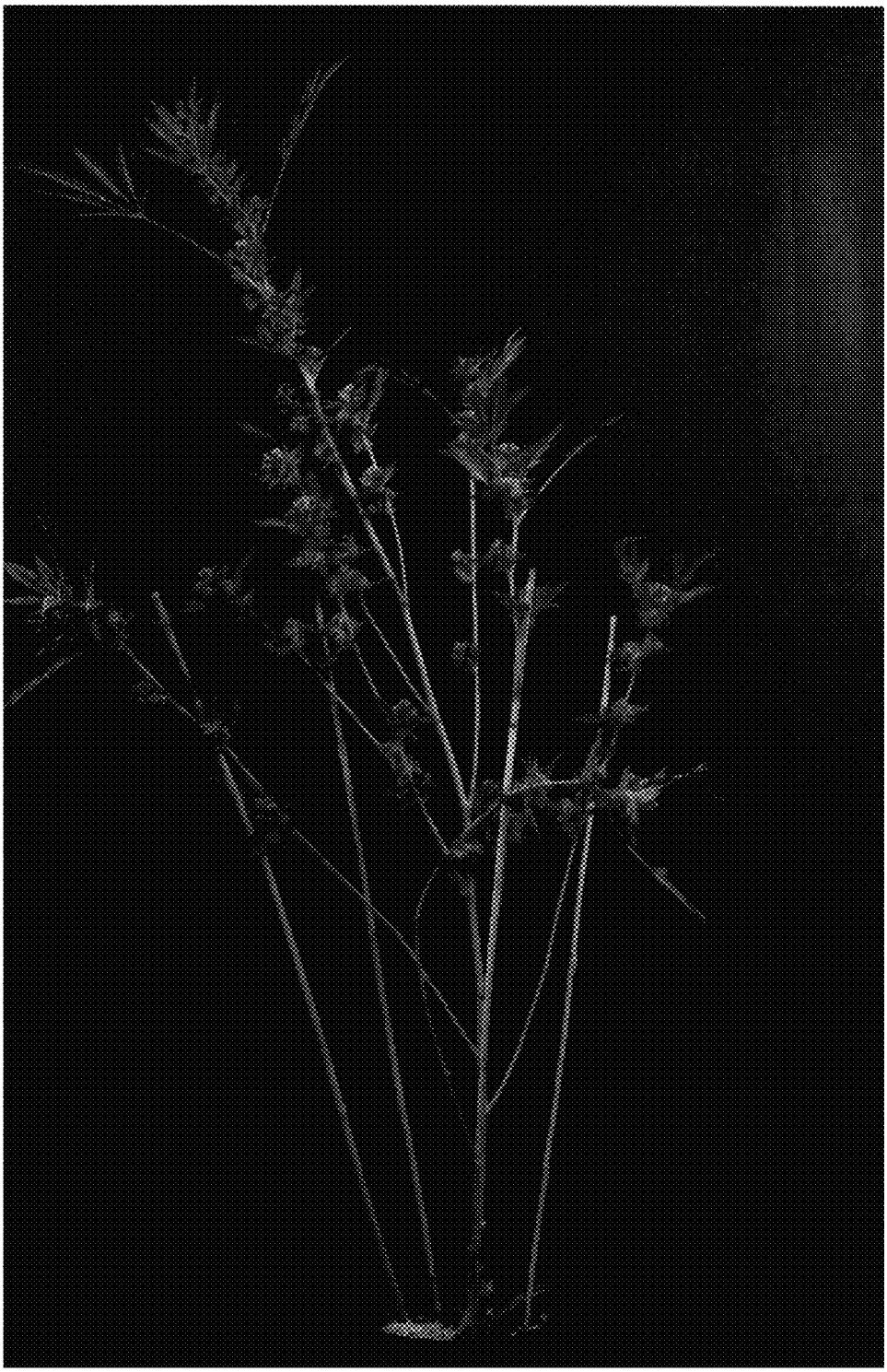
FIG. 1B illustrates a side view of another 'D1117' plant.
Figure 2A:
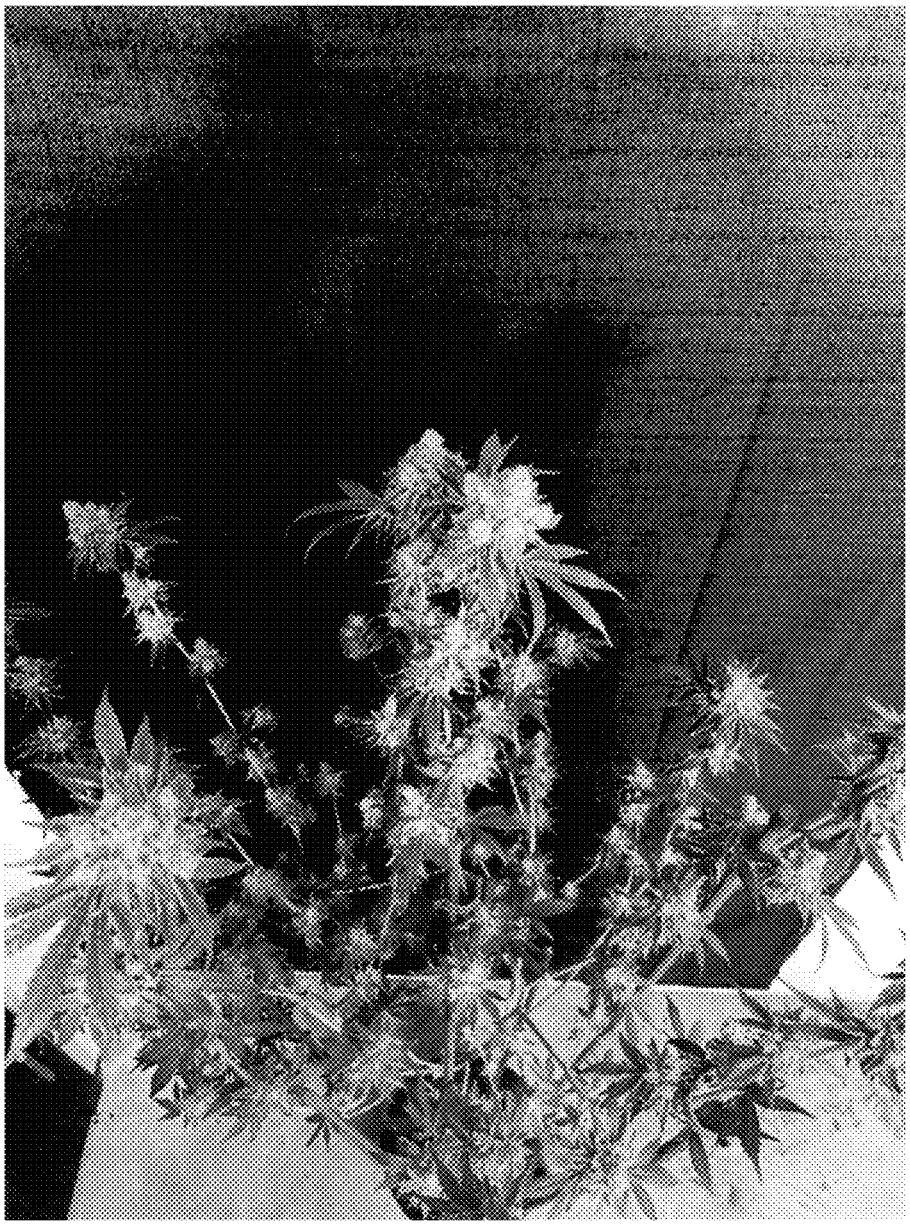
FIG. 2A illustrates a top view of a whole 'D1117' plant.
Figure 2B:
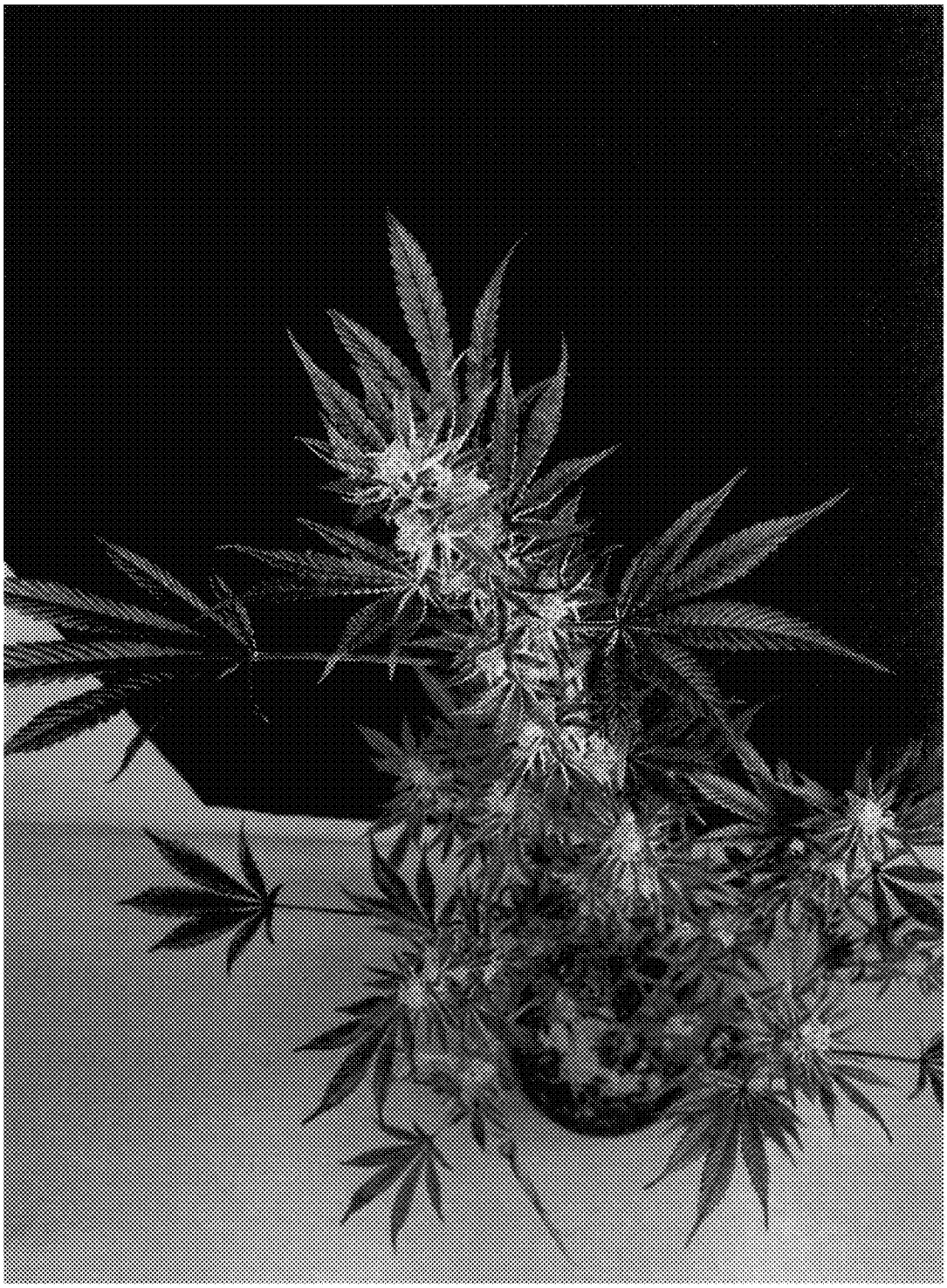
FIG. 2B illustrates a top view of another whole 'D1117' plant.
Figure 3:
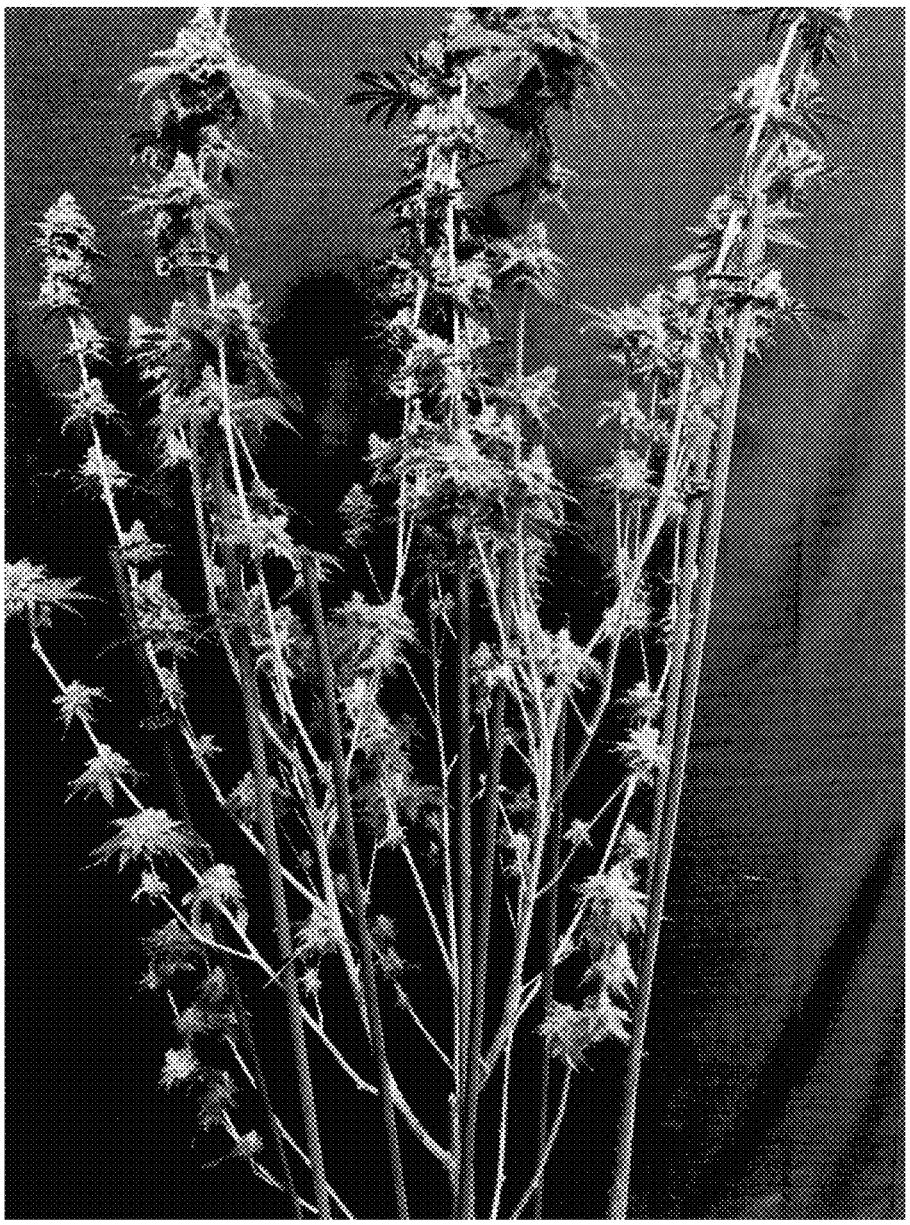
FIG. 3 illustrates branching patterns of a 'D1117' plant.
Figure 4A:
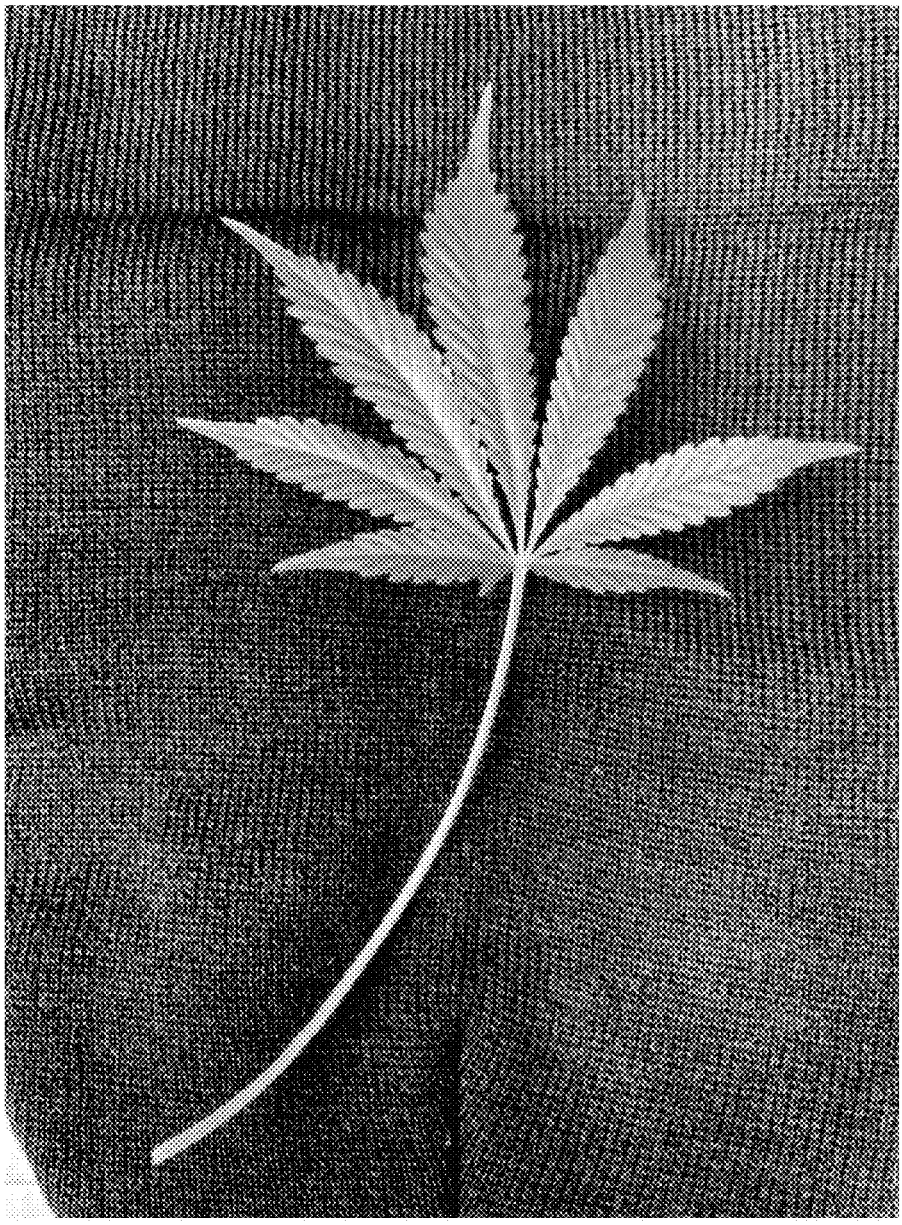
FIG. 4A illustrates the leaf shape and color of a 'D1117' plant.
Figure 4B:
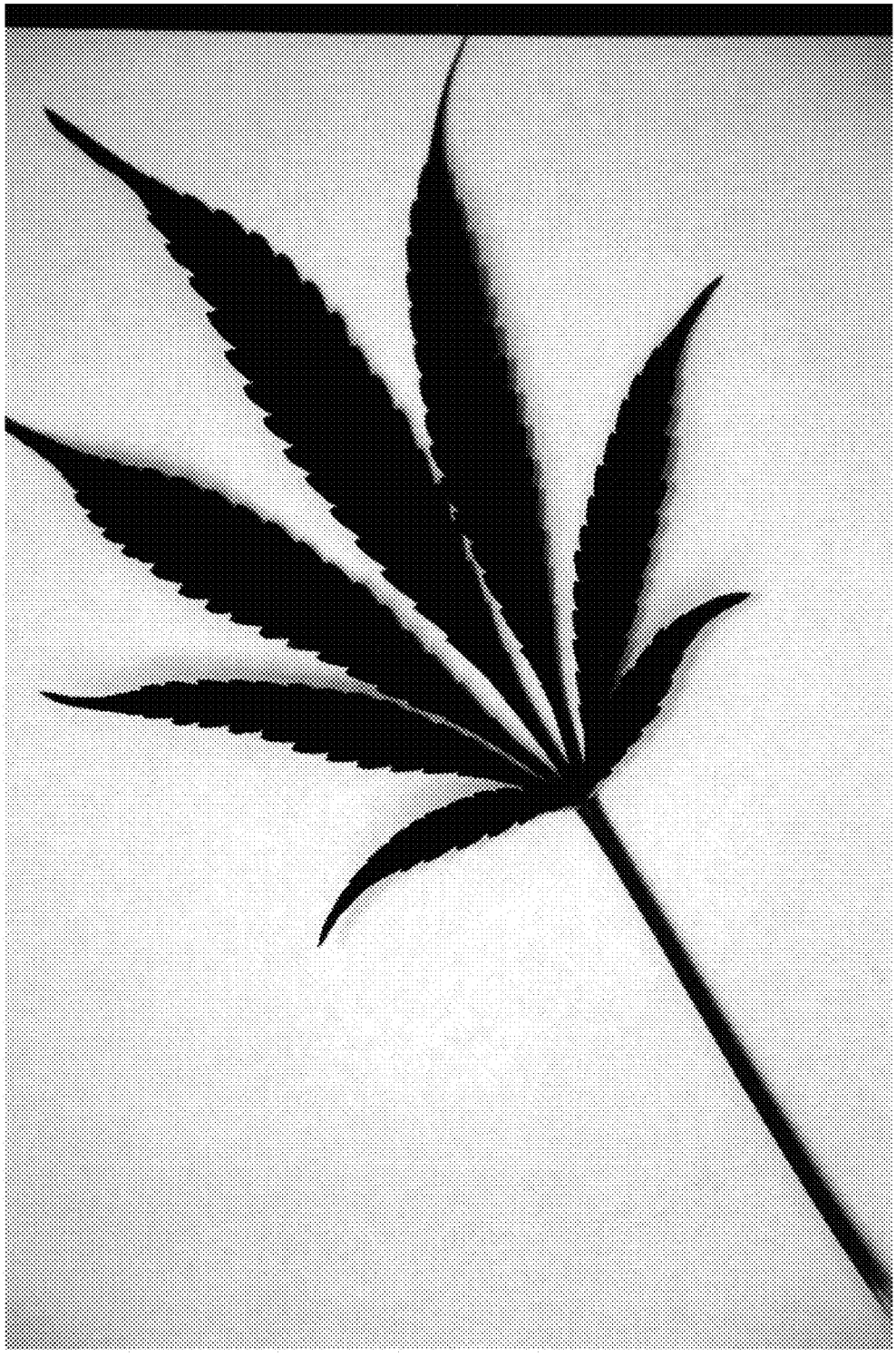
FIG. 4B illustrates another leaf shape and color of 'D1117'.
Figure 5A:
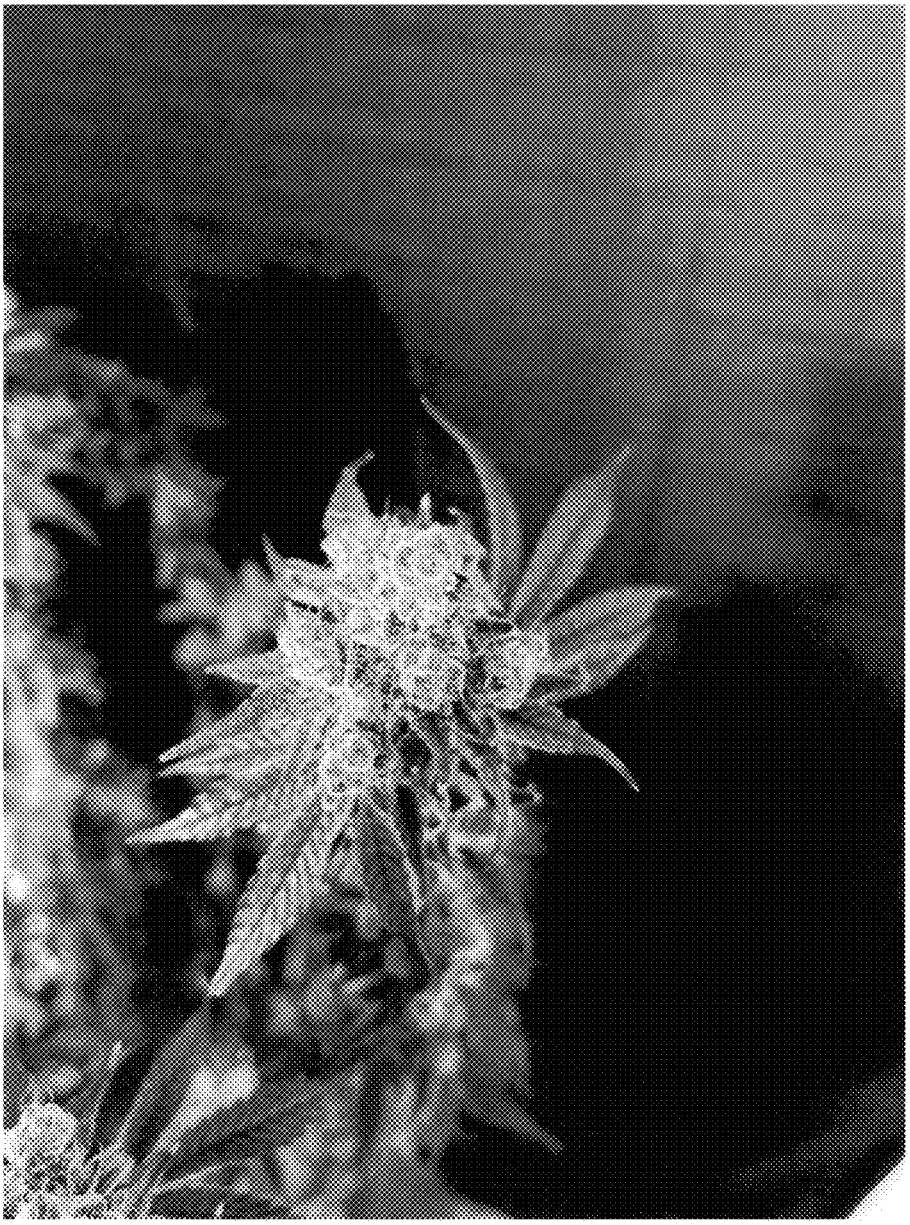
FIG. 5A illustrates a top view of a flower of 'D1117' plant.
Figure 5B:
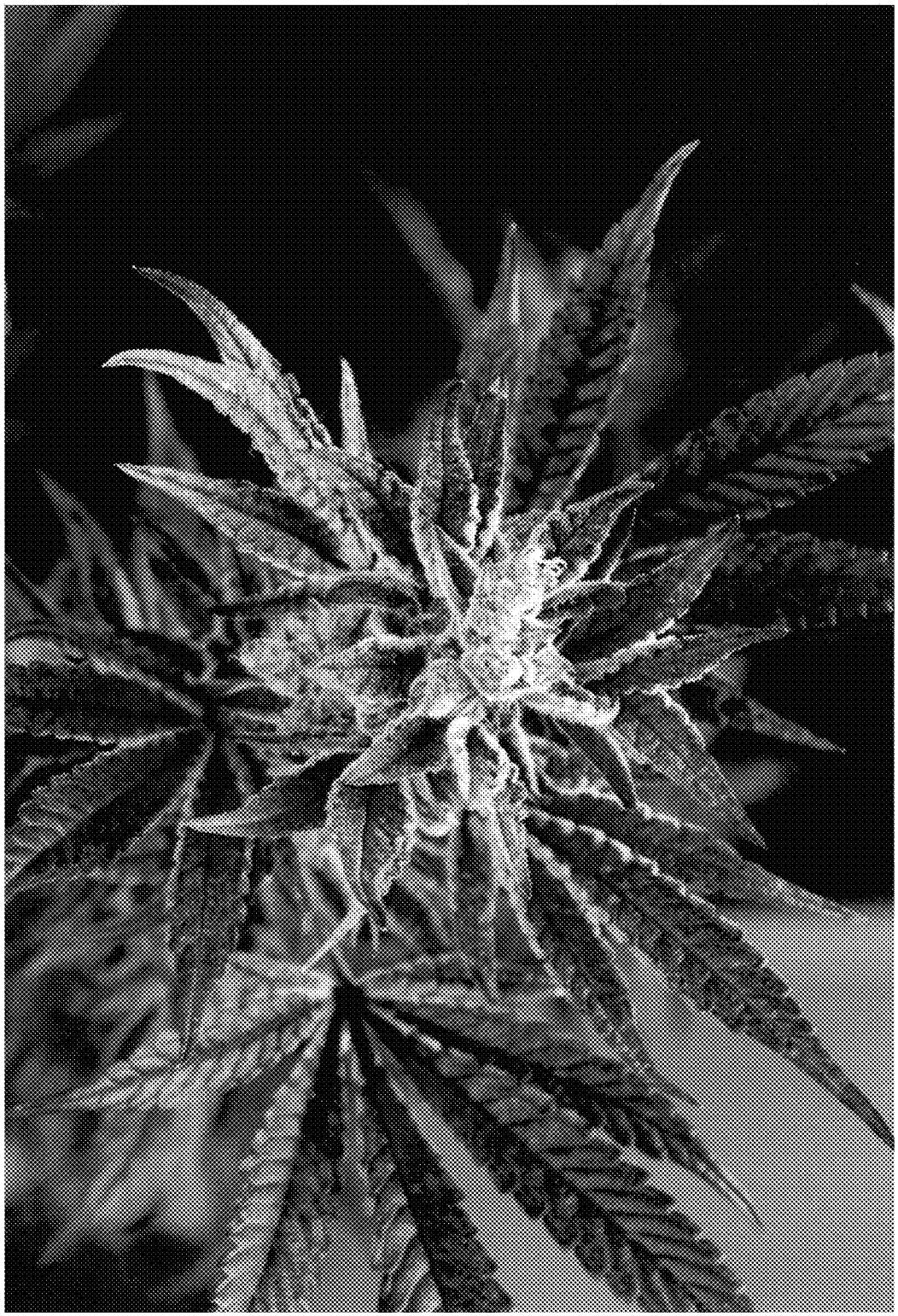
FIG. 5B illustrates a top view of a flower of another 'D1117' plant.
Figure 6A:
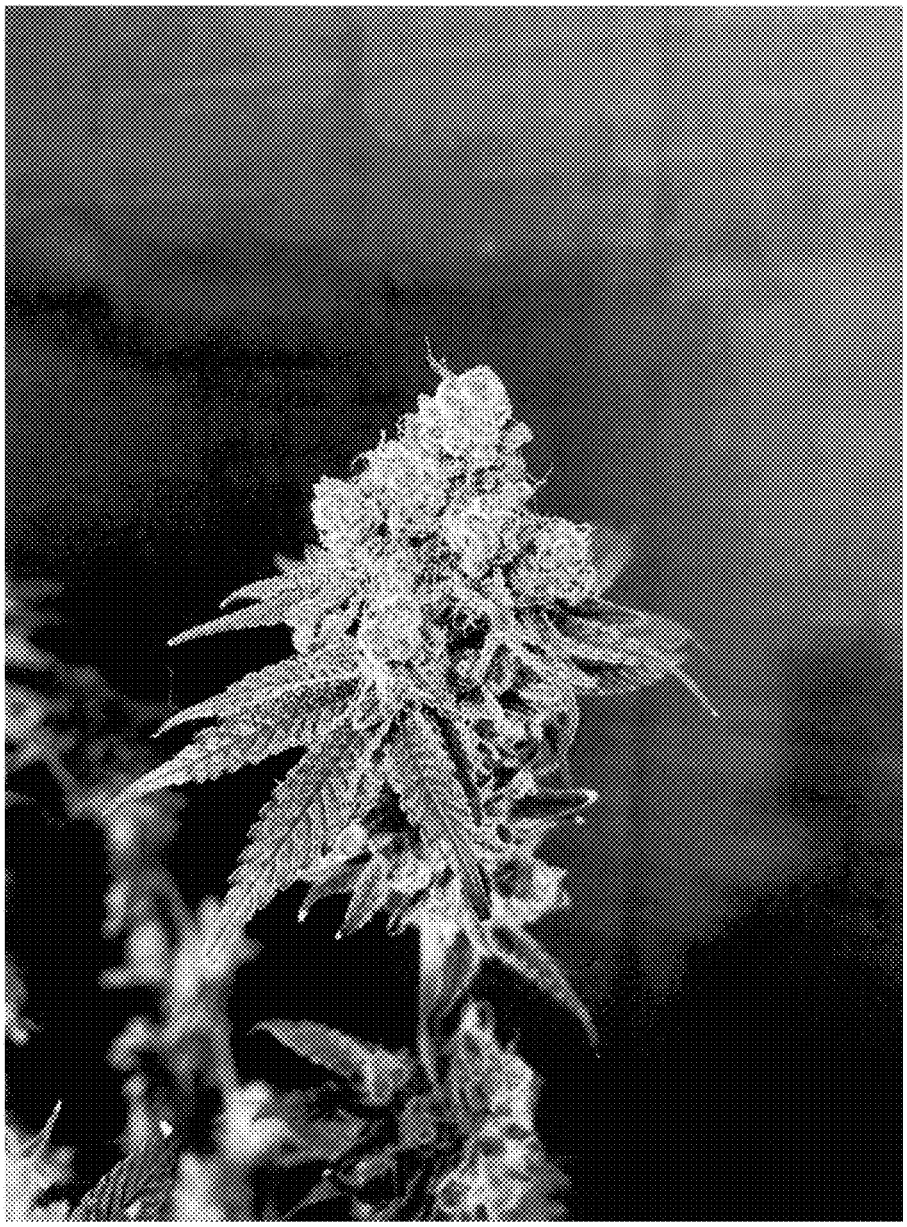
FIG. 6A illustrates a close-up side view of a flower of a 'D1117' plant.
Figure 6B:
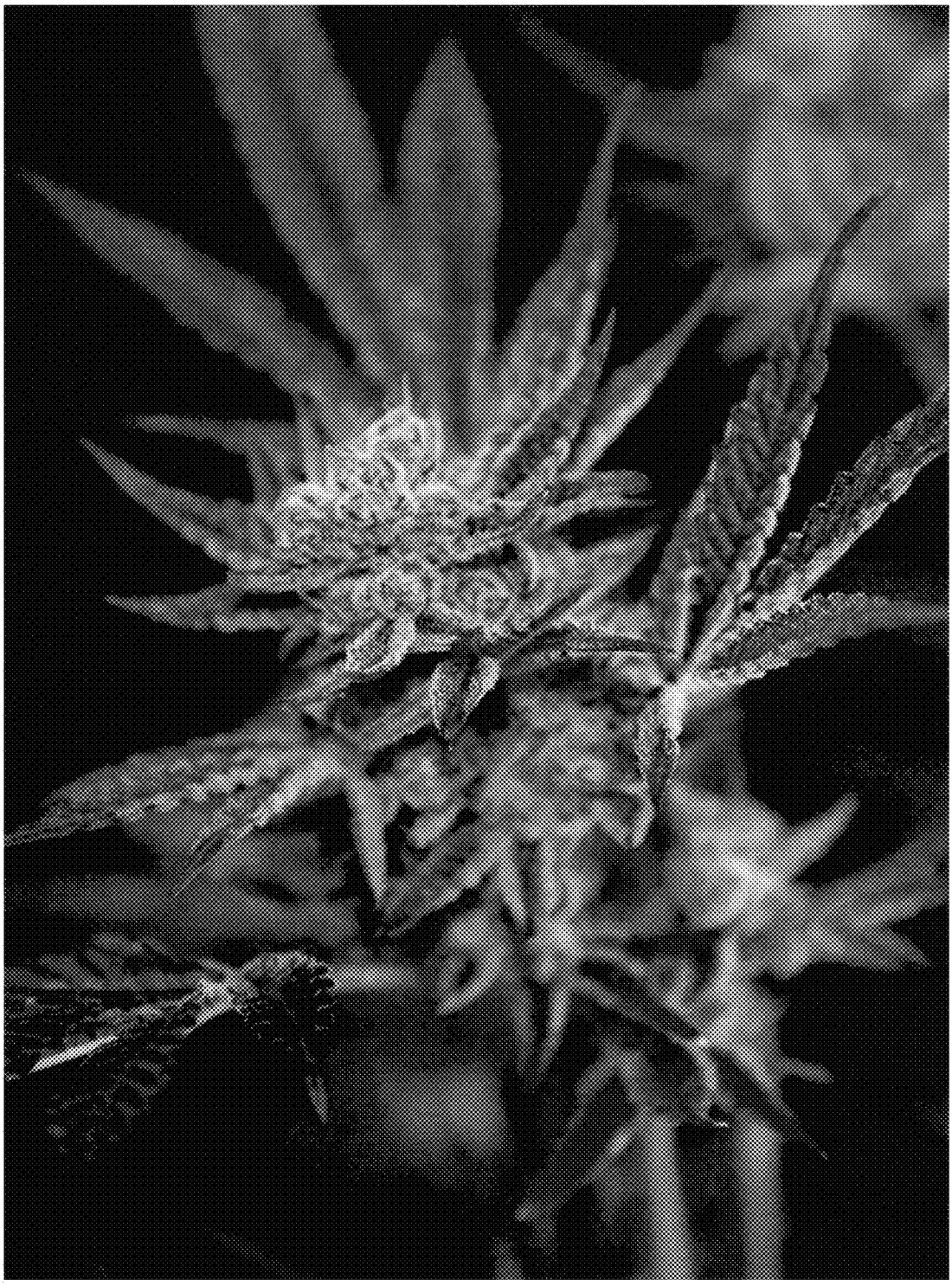
FIG. 6B illustrates a close-up side view of a flower of another 'D1117' plant.
Figure 7A:
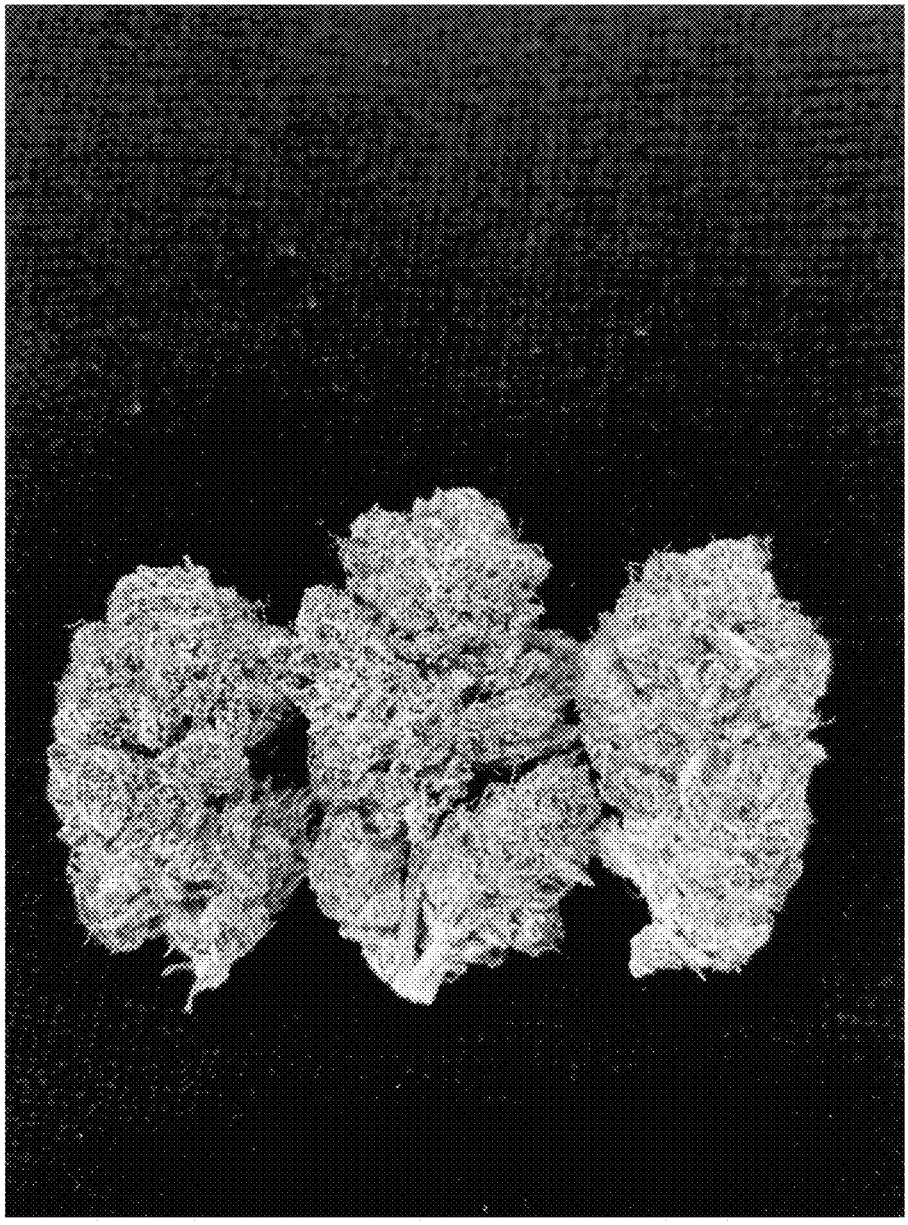
FIG. 7A illustrates dried flower buds of a 'D1117' plant.
Figure 7B:
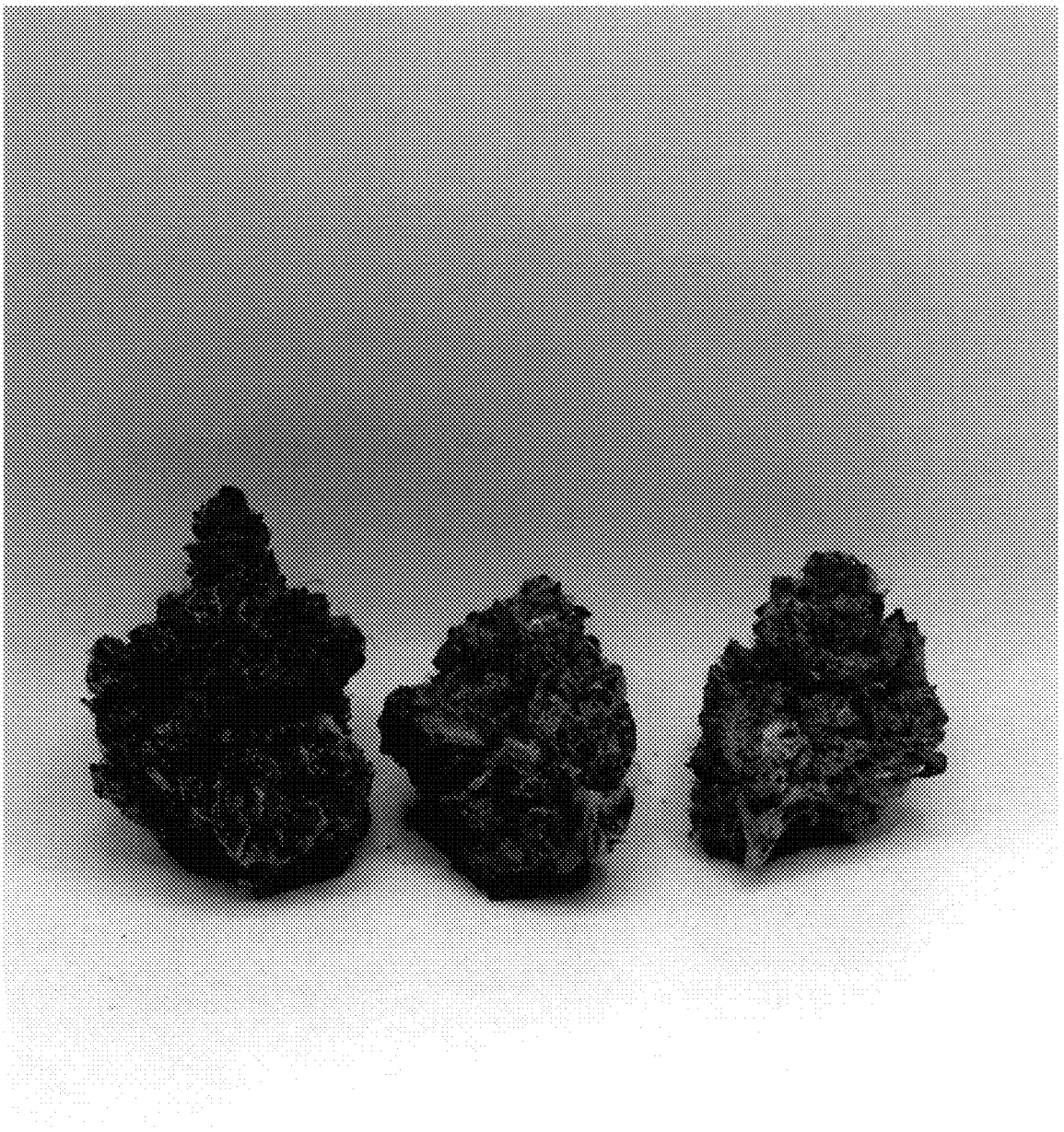
FIG. 7B illustrates dried flower buds of another 'D1117' plant.

The following description sets forth the distinctive characteristics of 'D1117'. The data that define these characteristics are based on observations taken from plants grown in greenhouses in Pullman, WA. USA, from June 2022 to September 2022. The growth conditions were as follows (averages and standard deviation for 8 weeks of growth): temperature of 78±5 F (day) and 68±7 F (night); relative humidity of 60±9% (day) and 64±7% (night). Color designations, color descriptions, and other phenotypical descriptions may deviate from the stated values and descriptions depending upon variation in environmental, seasonal, climatic, and cultural conditions. 'D1117' has not been observed under all possible environmental conditions. Unless noted otherwise, the botanical description of 'D1117' was taken from plants 8 weeks after changing from a 18 h light/6 h dark lighting regime to a 12 h light/12 h dark lighting regime. The indicated values represent averages calculated from measurements of 180 plants after 2 growing cycles, unless otherwise indicated. Color references are primarily provided in hexadecimal code, also known as hex color code, hex code, or HTML color code. Hexadecimal code is understood in the art and follows defined rules as described in, for example, history-computer[dot]com/hex-code-html-color-codes/ and codeconquest[dot]com/hex-color-codes. Descriptive terminology follows the *Plant Identification Terminology, An Illustrated Glossary*, 2nd edition by James G. Harris and Melinda Woolf Harris, unless where otherwise defined.

Classification:

*Family.*—Cannabaceae.

*Species.*—*Cannabis* hybrid.

*Denomination.*—'D1117'.

Parentage:

*Female parent.*—'Mango Sherbet' (unpatented).

*Male parent.*—'Purple Tahoe' (unpatented).

Propagation:

*Propagation method.*—Clonal.

*Time to produce a rooted young plant.*—1.5 days.

Plant (at flowering stage):

*Height.*—119 cm.

*Width.*—81 cm.

*Vigor.*—Strong.

*Branching.*—Strong lateral branching pattern with many branch points per stem.

*Branching angle.*—40 degrees.

*Intensity of anthocyanin coloration of crown* (*where stem meets roots*).—Absent.
*Proportion of hermaphrodite plants.*—Low to zero in optimal growing conditions.
*Proportion of male plants.*—Low to zero in optimal growing condition.

Stem (at flowering):
*Height.*—76 cm.
*Diameter at base.*—2.87 cm.
*Color.*—#C3D07A (light yellow-green).
*Depth of ribs or grooves.*—Shallow.
*Texture.*—Smooth.
*Internode length.*—4.1+/31 0.95 cm (average individual internode values from 3 different plants, +/− standard deviation. representative of internodes from the main stem of the entire plant).
*Number of internodes.*—14.
*Amount of pith in main stem cross-section.*—Thick.
*Stem trichrome type.*—Nonglandular — Cystolithic.

Fan leaves (at flowering stage):
*Length.*—11.57 cm (includes petiole).
*Width.*—6.2 cm.
*Texture on upper surface.*—Smooth.
*Texture on lower surface.*—Veined.
*Shape.*—Palmately compound.
*Margin.*—Serrate.
*Vein color.*—#A8A499 (yellow-green-gray).
*Color on upper side.*—Ranging from #81BA12 (light green) to #3B3236 (dark purple).
*Color on lower side.*—Ranging from #D5D7AC (light green-tan) to #625C45 (brown).
*Number of leaflets.*—7.
*Leaflet margin.*—Serrate.
*Leaflet shape.*—Lanceolate.
*Leaflet apex shape.*—Attenuate.
*Leaflet base shape.*—Attenuate.
*Central leaflet length.*—6.63 cm.
*Central leaflet width.*—1.37 cm.
*Trichome types.*—Glandular — Capitate stalked. Nonglandular — Cystolithic.
*Immature trichome color.*—#FFF9E3 (clear/white).
*Mature trichome color.*—#A76426 (amber/brown).

Petiole (at flowering stage):
*Length.*—49.67 mm.
*Diameter.*—2.0 mm.
*Color.*—Ranging from #F3FF6C (bright yellow-green) to #513A39 (brown).
*Intensity of anthocyanin coloration.*—Ranging from weak to strong.
*Stipule color.*—Ranging from #E3F15D (bright yellow-green) to #543A0E (brown).
*Stipule shape.*—Acicular.
*Stipule site.*—9.25 mm.
*Trichome type.*—Nonglandular — Cystolithic.

Sugar leaves:
*Length.*—3.23 cm.
*Width.*—2.5 cm.
*Texture on upper surface.*—Smooth.
*Texture on lower surface.*—Veined.
*Shape.*—Palmately compound.
*Margin.*—Serrate.
*Vein color.*—#A8A499 (yellow-green-gray).
*Color on upper side.*—Ranging from #81BA12 (light green) to #3B3236 (dark purple).
*Color on lower side.*—Ranging from #D5D7AC (light green-tan) to #625C45 (brown).
*Number of leaflets.*—7.
*Leaflet margin.*—Serrate.
*Leaflet shape.*—Lanceolate.
*Leaflet apex shape.*—Attenuate.
*Leaflet base shape.*—Attenuate.
*Central leaflet length.*—2.2 cm.
*Central leaflet width.*—0.8 cm.
*Trichome type.*—Glandular — Capitate stalked.
*Immature trichome color.*—#FFF9E3 (clear/white).
*Mature trichome color.*—#A76426 (amber/brown).

Flowers (at flowering stage):
*Flowers per plant.*—2,500-3,000.
*Flower length.*—30.67 mm.
*Flower diameter.*—24.0 mm.
*Color.*—Mix of #92B05F (light green), purple, orange, and brown.
*Aroma.*—Floral, sweet, mango; rich in caryophyllene, limonene, farnesene, linalool, pinene, and terpineol.
*Structure.*—Composed of block-shaped calyxes forming a round flower shape.
*Shape.*—Calcarate-urceolate; small green bract enclosing the ovary with two slender stigmas, without petals or sepals.
*Calyx structure.*—Block-like.
*Trichome density.*—High.
*Bract length.*—9.25 mm.
*Bract width.*—7.50 mm.
*Bract shape.*—Acuminate.
*Average number of bracts per compound flower.*—24.
*Bract color.*—Mix of #C9DD9F (lime), purple, orange, and brown.
*Bract trichome type.*—Glandular — Capitate stalked.
*Immature bract trichome color.*—#FFF9E3 (clear/white).
*Mature bract trichome color.*—#A76426 (amber/brown).
*Bracteole length.*—9.25 mm.
*Bracteole width.*—3.75 mm.
*Bracteole shape.*—Acuminate.
*Average number of bracteoles per compound flower.*—48.
*Bracteole trichome type.*—Glandular — Capitate stalked.
*Immature bracteole trichome color.*—#FFF9E3 (clear/white).
*Mature bracteole trichome color.*—#A76426 (amber/brown).
*Average number of stigmas per compound flower.*—48.
*Stigma length.*—7.7 mm.
*Immature stigma color.*—#EBCB90 (light yellow).
*Mature stigma color.*—#DEAA68 (orange).
*Stigma trichrome types.*—Glandular — Capitate stalked. Nonglandular — Cystolithic.
*Stigma trichome color.*—Clear/white.

Flowers (dried):
*Productivity.*—approximately 1.40 g of dry flower material (under optimal greenhouse conditions).
*Shipping quality.*—Good.
*Storage life.*—Good.

Chemotypic characteristics:
*Method of determination.*—HPLC as described in Zager et al. (2019, Plant Physiol. 180(4): 1877-1897).

*THC content.*—22.21% by weight.

*CBD content.*—0.10% by weight.

*CBG content.*—Not detected.

Terpene content:

*Method of determination.*—GC/MS as described in Zager et al. (2019, Plant Physiol. 180(4).—1877-1897).

*Beta-Caryophyllene.*—7.48 mg/g.

*Limonene.*—3.00 mg/g.

*Alpha-Farnesene.*—1.27 mg/g.

*Alpha-Bisabolol.*—1.21 mg/g.

*Aromadendrene.*—0.93 mg/g.

Seeds:

*Seed length.*—5.45 mm.

*Seed width.*—4.12 mm.

*Seed color.*—#635C3F (light brown) and #342F1B (dark brown) marbled.

Pest and pathogen resistance/susceptibility: Contains the dominant resistant allele of the powdery mildew resistance gene 'PM1' characterized in Mihalyov and Garfinkel (2021, Front. Agron. 3: 720215), providing resistance at least to powdery mildew caused by the fungal pathogen *Golovinomyces ambrosiae*. No powdery mildew infections have been documented on 'D1117'.

COMPARISONS TO PARENTAL AND REFERENCE VARIETIES

'D1117' differs from the female parent 'Mango Sherbet' (unpatented) in that 'D1117' displays considerably increased lateral branching patterns and has larger flower structure compared to 'Mango Sherbet'. In addition, 'D1117' differs in its aromatic profile from 'Mango Sherbet'.

'D1117' differs from the male parent 'Purple Tahoe' (unpatented) in that 'D1117' has fewer leaf points than 'Purple Tahoe'. In addition, 'D1117' differs in its aromatic profile from 'Purple Tahoe'.

'D1117' differs from the reference variety 'Purple Punch' (unpatented) in that 'D1117' has a sweeter aroma profile, displays a block-like calyx structure, and has a deeper coloration of leaf tissue compared to 'Purple Punch'.

'D1117' differs from the reference variety 'G13' (unpatented) in that 'D1117' displays a vastly different terpene profile, has denser flower production, and displays increased trichrome density in its flowers relative to 'G13'.

What is claimed is:

1. A new and distinct variety of *Cannabis* plant designated 'D1117' as shown and described herein.

* * * * *